(12) United States Patent  
Zou

(10) Patent No.: US 8,031,831 B2  
(45) Date of Patent: Oct. 4, 2011

(54) VOLTAGE AND OR CURRENT MODULATION IN DUAL ENERGY COMPUTED TOMOGRAPHY

(75) Inventor: Yu Zou, Naperville, IL (US)

(73) Assignees: Kabushiki Kaisha Toshiba, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 0 days.

(21) Appl. No.: 12/473,820

(22) Filed: May 28, 2009

(65) Prior Publication Data
US 2010/0303196 A1 Dec. 2, 2010

(51) Int. Cl.
*G01N 23/087* (2006.01)

(52) U.S. Cl. ........... 378/16; 378/5; 378/9; 378/98.9; 378/108; 378/111

(58) Field of Classification Search ........ 378/5, 15, 378/16, 9, 98.9, 108, 111
See application file for complete search history.

(56) References Cited

U.S. PATENT DOCUMENTS

| | | | | |
|---|---|---|---|---|
| 5,379,333 A | * | 1/1995 | Toth | 378/16 |
| 5,570,403 A | * | 10/1996 | Yamazaki et al. | 378/5 |
| 5,822,393 A | * | 10/1998 | Popescu | 378/108 |
| 5,949,811 A | * | 9/1999 | Baba et al. | 378/108 |
| 6,094,468 A | * | 7/2000 | Wilting et al. | 378/8 |
| 6,385,280 B1 | * | 5/2002 | Bittl et al. | 378/16 |
| 6,490,337 B1 | * | 12/2002 | Nagaoka et al. | 378/20 |
| 6,507,639 B1 | * | 1/2003 | Popescu | 378/108 |
| 7,085,343 B2 | * | 8/2006 | Shinno et al. | 378/9 |
| 7,486,763 B2 | * | 2/2009 | Popescu | 378/15 |
| 7,545,907 B2 | * | 6/2009 | Stewart et al. | 378/37 |
| 2009/0262997 A1 | | 10/2009 | Zou et al. | |
| 2010/0008465 A1 | * | 1/2010 | Matsuura et al. | 378/62 |
| 2010/0067647 A1 | * | 3/2010 | Bani-Hashemi et al. | 378/5 |
| 2010/0189212 A1 | | 7/2010 | Zou | |

FOREIGN PATENT DOCUMENTS

| | | |
|---|---|---|
| JP | 53-110495 A | 9/1978 |
| JP | 2704084 B2 | 11/1993 |

OTHER PUBLICATIONS

Hounsfield, G.N., Computerized transverse axial scanning (tomography): Part 1. Description of system, British Journal of Radiology, 46, 1016-1022 (1973).

Alvarez, R. and Macovski, A., "Energy-selective reconstruction in x-ray computerized tomography," Phys Med. Biol., 21(5), 733-744 (1976).

Zou, Yu, "Analysis of Fast kV-switching in Dual Energy CT using a Pre-construction Decomposition Technique", Proc. SPIE, vol. 6913, 691313 (2008).

Stenner, P. and Kachelrie, M., Dual energy exposure control (DEEC) for computed tomography: Algorithm and simulation study; Med Phys., 35(11), 5054-5060 (2008).

* cited by examiner

*Primary Examiner* — Edward J Glick  
*Assistant Examiner* — Thomas R Artman  
(74) *Attorney, Agent, or Firm* — Knoble Yoshida & Dunleavy, LLC

(57) ABSTRACT

To prevent patients from being overexposed or underexposed, it has been attempted to modulate either voltage or current in conventional single energy CT systems. The voltage modulation causes incompatibility in projection data among the views while the current modulation reduces only noise. To solve these and other problems, dual energy CT is combined with voltage modulation techniques to improve the dosage efficiency. Furthermore, dual energy CT has been combined with both voltage modulation and current modulation to optimize the dosage efficiency in order to minimize radiation to a patient without sacrificing the reconstructed image quality.

31 Claims, 13 Drawing Sheets

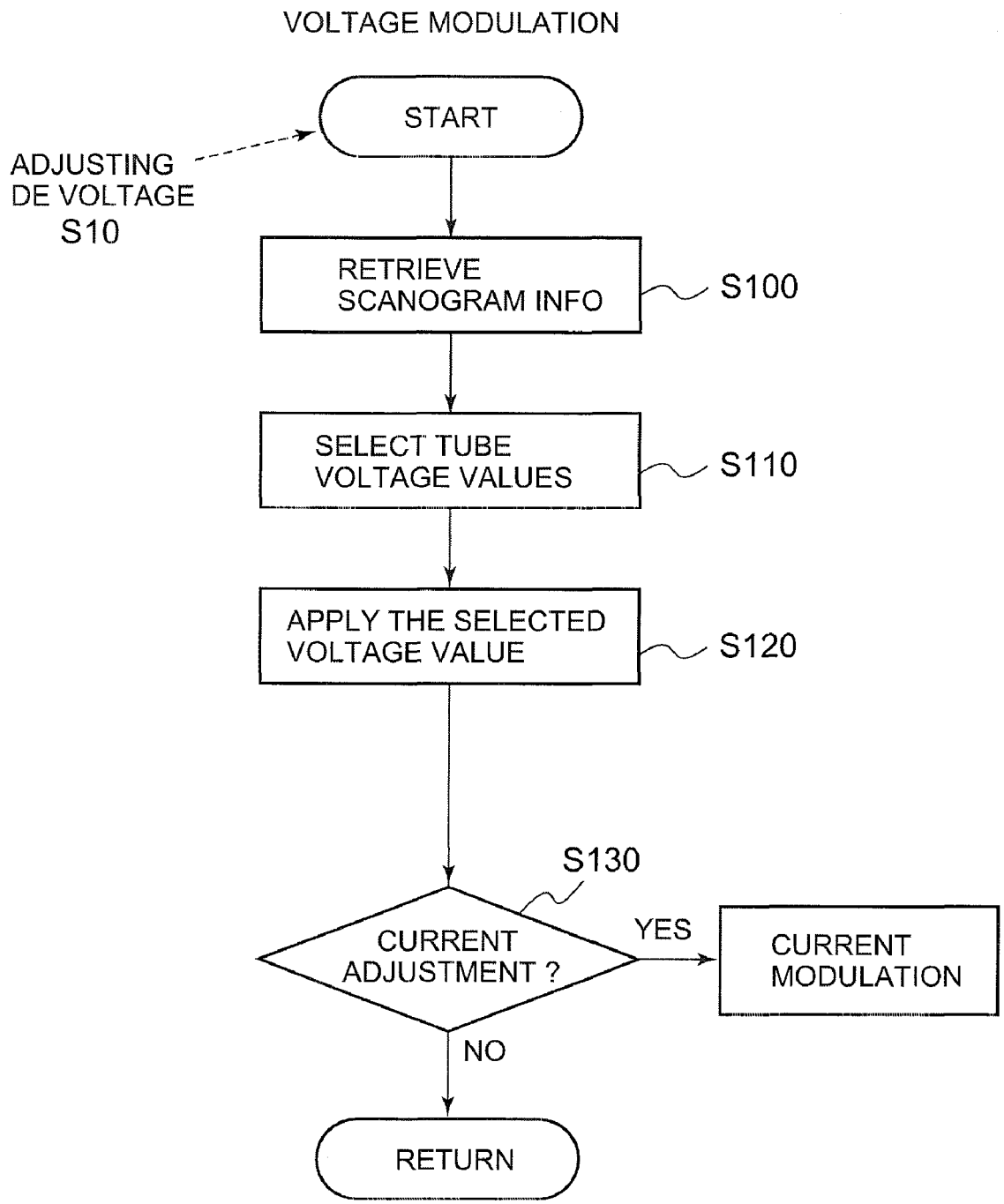

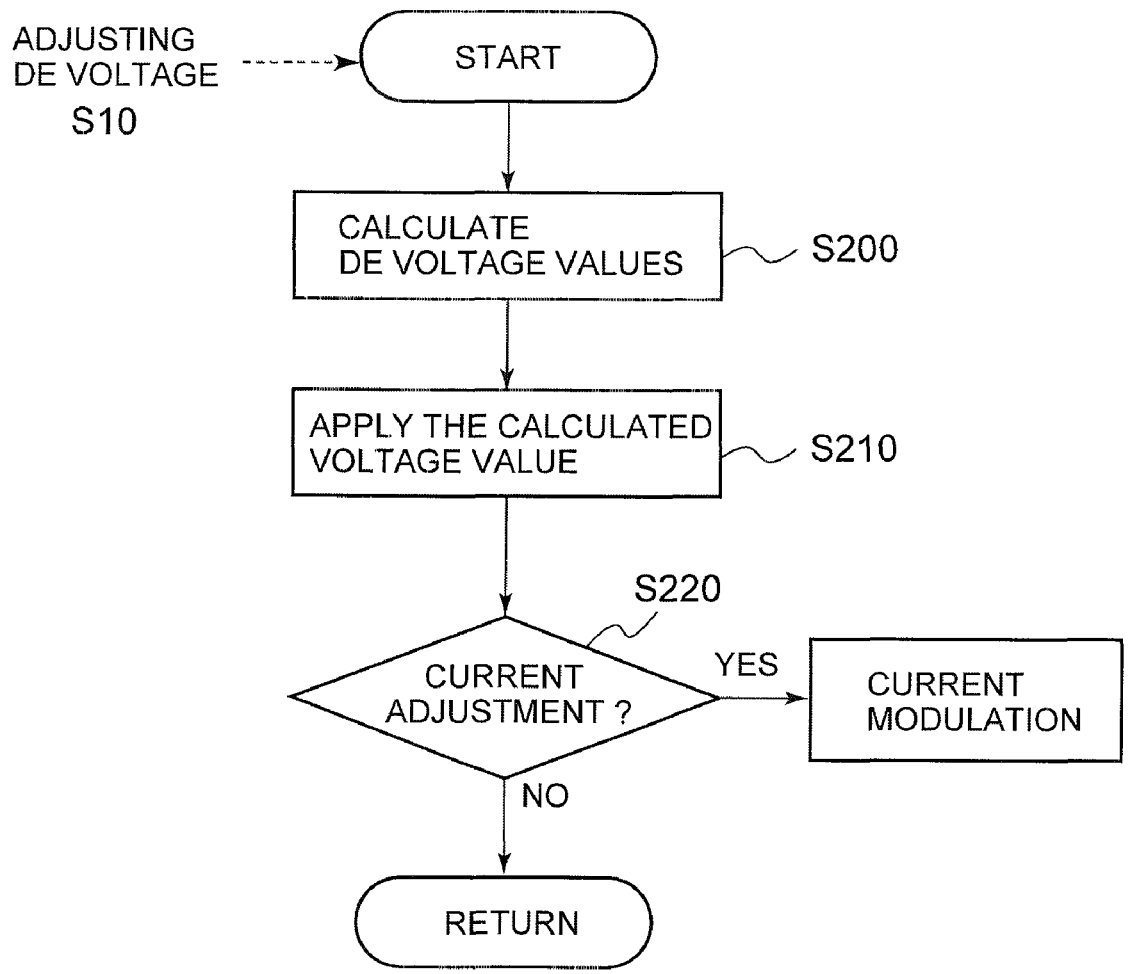

FIG. 6 CURRENT MODULATION
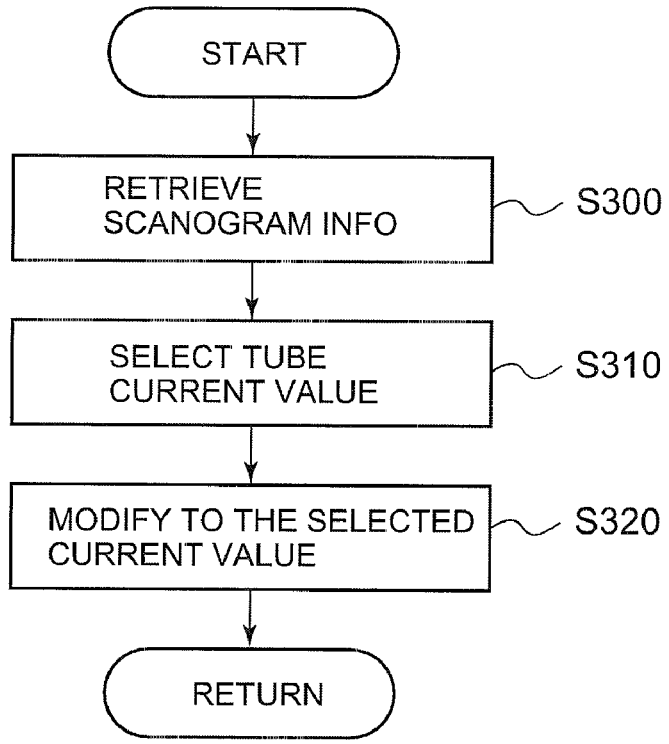
FIG. 7 CURRENT MODULATION
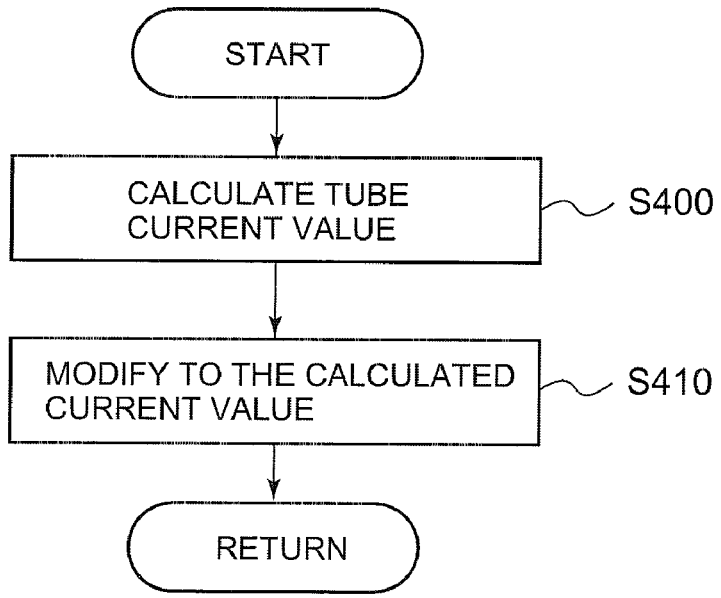

VOLTAGE AND OR CURRENT MODULATION IN DUAL ENERGY COMPUTED TOMOGRAPHY

FIELD OF THE INVENTION

The embodiments of the current invention are generally related to voltage and or current modulation in dual energy computed tomography (CT) and more particularly related to optimal dosage efficiency in obtaining projection data sets while patient dose exposure is reduced and reconstructed image quality is preserved.

BACKGROUND OF THE INVENTION

Conventional computed tomography (CT) systems with an X-ray tube operating at a constant voltage and a constant current face image-quality problems in scanning various parts of a patient in one acquisition or scanning one part where the attenuation strongly depends on a view angle. Since the physical dimensions of certain body parts significantly vary with respect to views, the transmitted X-ray attenuates at a different level. In other words, since a prior art X-ray energy source provides the same spectrum and flux of the X-ray beams to acquire projection data sets regardless of the physical dimensions of a scanned part, an image quality varies depending upon the physical dimension and other variables such as a material distribution. To improve image quality, as the voltage and current are fixedly increased with respect to large dimensional views, a patient is exposed to an unnecessary amount of high radiation while projection data are acquired from small dimensional views. On the other hand, as the voltage and current are fixedly decreased with respect to small dimensional views, image quality suffers from artifacts due to the poor quality of data from large dimensional views. The constant exposure level prevents the optimal data acquisition. Consequently, the patient may be either overexposed or underexposed during the data acquisition.

With respect to the above issue, prior art techniques modulated either a tube voltage or a tube current of a single energy X-ray source. For example, Japanese Patent Publication 53-110495 discloses that an amount of X ray at a detector is kept constant across various parts of the scanned body by modulating the tube voltage based upon a feedback signal from the X-ray detector. In other words, assuming the same X-ray attenuation coefficient through various parts of a different thickness, a large amount of high-energy X ray is projected into a thicker portion while a small amount of low-energy X ray is projected into a thinner portion so that the attenuated x-radiation is constant at the detector across the various portions via a feedback control.

The above prior art technique assumes the constant attenuation coefficient across various parts of the patient body. In contrast to the assumption, various body parts have a different attenuation profile. Furthermore, the voltage is modulated while the scanning process is taking place. In other words, since the voltage is being modulated at various angles about the scanning axis and also at various positions along the same scanning axis, the acquired projection data are not compatible with each other for the image reconstruction processes. For example, for a given projection, there is only a single set of projection data at a particular voltage level, and this projection data cannot be generally combined with another set of projection data at a different energy level due to the energy-dependent nature of the attenuation coefficient. Consequently, image reconstruction fails to yield a desirably artifact-free image.

In this regard, Japanese Patent 2704084 discloses that an attenuated X-ray level is kept substantially constant at various angles and positions along the scanning direction by modulating a tube current level. In order to accomplish the substantial consistency, an attenuated x-radiation value at the present angle and position is approximated to an average attenuated x-radiation value at the previously detected angle and position based upon current modulation. In other words, the tube voltage is kept constant throughout the scanning process while the tube current alone is modulated to avoid the above described projection data incompatibility.

The current modulation is generally useful in controlling the noise level but not the penetration of x-ray beam that relates to the dose efficiency. Roughly speaking, the higher a tube current level is during the projection data acquisition, the lower a noise level becomes in the acquired projection data sets. More precisely, the noise level, variance of the projection data, is inversely proportional to the current level. On the other hand, the tube current is proportional to the dosage to the patient. In this regard, the current modulation may improve image quality and achieve an optimal dosage level in the case of fixed dose efficiency. However, the optimal dosage level can be further reduced by improving the dose efficiency through adjusting the penetration of X-ray beam.

In order to improve the patient safety, an optimal dose efficiency level must be achieved during the CT scanning procedure. That is, the patient is exposed to a minimally necessary radiation level while the image quality in the reconstructed image is not sacrificed. The dose efficiency is generally defined to be $(S/N)^2$ divided by a dose level, where $(S/N)$ is a signal-to-noise ratio. The dose efficiency depends on x-ray spectrum, detector characteristics and attenuation of the imaged subject. Thus, an optimal dose efficiency level is obtained for a particular material of a certain physical size by controlling the spectrum through the tube voltage modulation.

From the above background information, it appears necessary to modulate the tube voltage level in order to optimize the dose efficiency level since a current modulation alone does not achieve the ultimate goals both in patient safety and image quality. On the other hand, from the prior art attempts, the voltage modulation has an inherent issue of data incompatibility among the projection data if images are reconstructed with a single energy CT reconstructor. In this regard, more recent prior art techniques involve dual energy imaging techniques.

Dual energy imaging in CT has been a promising technique since the first days of CT and was even mentioned in Godfrey Hounsfield's paper (1973) that introduced CT. The basic idea is to acquire two data sets at low and high energy levels and to use the pairs of the data sets to deduce additional information about the patient.

The physical basis of dual energy imaging includes two main mechanisms of the interaction of X rays with matter in the clinically relevant diagnostic energy-range from 30 keV to 140 keV, and the two interactions are photoelectric absorption and Compton scattering, each having its own functional dependence on X-ray energy. Photoelectric absorption is a rapidly decreasing function of energy while Compton scatter is a gentle function of energy. As shown in FIG. 1, the photoelectric interaction is a strong function of the effective atomic number (Z) of the absorbing tissue while scattering is nearly independent of Z. The physics enabled Alvarez and Macovski (1976) to develop a mathematical scheme, called dual-energy decomposition, to use the dual energy information.

In addition to the energy dependence, dual-energy decomposition must take X-ray sources into account. Since commercial clinical CT-scanners generally use polychromatic sources, the mathematics of dual energy imaging is not trivial. In this regard, single-energy imaging with a polychromatic source does not have an exact and analytic solution. One mathematical approach in dual-energy decomposition using a polychromatic source has been described in a related U.S. application Ser. No. 12/361,280 filed on Jan. 28, 2009 and Ser. No 12/106,907 filed on Apr. 21, 2008 as well as in a reference entitled as "Analysis of Fast kV-switching in Dual Energy CT using a Pre-reconstruction Decomposition Technique," by Yu Zou and Michael D. Silver (2009). In dual energy computed tomography (CT), fast kV-switching techniques generally alternate voltages between projections (also called views) so that the odd (or even) projections correspond to the low (or high) tube voltage. These references are incorporated into the current application by external reference to supplement the specification. Instead of the polynomial approximation method, in the previously proposed approach combining a linear term with a non-linear beam hardening term, an iterative solution to the dual energy data domain decomposition converges rapidly due to the dominant linear term.

In the past two years, prior art attempts have implemented certain dual energy CT systems. For example, Siemens has installed a number of dual source CT-scanners, which is equipped with two X-ray sources, and each runs at a different energy level for generating the two data sets. Another example is that Philips at their Haifa research facility has developed a sandwich detector where the upper layer records the low energy data and the lower layer records the high energy data. A prototype system is installed at the Hadassah Jerusalem Hospital. In this regard, GE has developed a specialized detector using garnet for capture 2496 total projections per rotation (TPPR) at a high speed. The fast detector has been combined with a fast kV-switching X-ray source to acquire the low and high energy data sets.

TABLE 1 below summarizes advantages and disadvantages of selected ways to acquire dual energy data sets. Fast kV-switching techniques change voltages between projections (also called views) so that the odd and even projections respectively correspond to the low or high tube voltage. Among these prior art approaches, the fast kV-switching appears an attractive technique for dual energy acquisition for a number of reasons. Since the dual source CT-scanners and the sandwich detector CT-scanners respectively require additional costs for the dual X-ray sources and the sandwich detectors, they may not be cost-effective to obtain dual energy data sets. Similarly, although GE's detector for fast kV-switching energy CT is not summarized in TABLE 1, the semi-precious gem detector also incurs additional costs. In addition, both the dual source CT-scanners and the sandwich detector CT-scanners must resolve other technical difficulties that are associated with these systems as listed in the table below. On the other hand, although the slow kV-switching does not require additional parts or equipment, dual energy data sets result in poor temporal registration that is off by at least one rotation period as well as poor spatial registration in particular from helical scans. For these reasons, the prior art technologies remain to find a cost effective system and method to utilized the dual energy data for CT.

TABLE 1

| Options | Advantages | Disadvantages |
| --- | --- | --- |
| Fast kV-switching (alternating views) | Temporal and spatial registration very good. Data domain methods possible leading to better IQ and flexibility. Helical acquisition no problem. | Limited energy separation unless square-wave waveform developed. Difficult to equalize dose/noise between high/low data sets. Development time and cost for fast, switching HVPS. |
| Slow kV-switching (alternating rotations) | Good energy separation. Easy to equalize dose/noise between high/low data sets. Little equipment development necessary. Little or no added H/W costs. | Poor temporal registration; off by at least one rotation period. Poor spatial registration, especially if doing helical scans and thus limited to image domain methods. Helical scans may require lower pitch and thus more dose. |
| Dual source | Good energy separation. Easy to equalize dose/noise between high/low data sets. | Temporal registration off by ¼ of the rotation period. Spatial registration requires tube alignment. Cost of two imaging chains. Field-of-view for dual energy limited by the smaller of the two imaging chains. Cross-scatter contamination. |
| Sandwich detector | Perfect temporal and spatial registration. Data domain decomposition methods valid. Helical acquisition no problem. | Limited energy separation. Cost and development of the detector. |

As already shown in TABLE 1, prior art fast kV-switching techniques without the use of dual sources or special detectors nonetheless have both advantages and disadvantages in acquiring dual energy data sets. The prior art fast kV-switching techniques have very good temporal and spatial registrations between corresponding high and low energy projections, which make data domain methods possible and lead to better IQ and flexibility. In addition, prior art fast kV-switching techniques acquire good dual energy data sets also through helical projections. A disadvantage is the one view misregistration between corresponding high and low energy projections. Another problem is the difficulty of high noise in the low energy data because it may be technically difficult to swing the mA as fast as the kV.

Regardless of the clinical significance, several hurdles remain for successful dual energy imaging. One important image quality issue is related to the different dose and noise levels between the two data sets. Depending on how the dual energy is achieved, the low energy data set could be very noisy compared with the high energy data set because X-ray tubes are less efficient at lower voltages, and the lower energy X rays usually have worse penetration in tissues, which will be a problem for larger patients. The same issue may be also problematic with scanning various parts of the same patients since the physical dimensions of these body parts significantly vary.

With respect to dual energy CT, one algorithm is described to modulate a current level in "Dual energy exposure control (DEEC) for computed tomography: Algorithm and simulation study," Phillip Stenner and Marc Kachelrie, Med. Phys. 35 (11), November 2008. The prior art technique claims that DEEC minimizes the noise in the final monochromatic image while it keeps the dose constant. Alternatively, the prior art technique claims that DEEC minimizes the dose while it keeps the noise constant. In other words, either the dose or the noise is improved by the current modulation in the above DEEC. In this regard, the prior art DEEC still fails to improve the dose efficiency.

Despite the above described prior art techniques, patient safety from X-ray overdose remains to be improved without sacrificing image quality. The advantages of dual energy CT includes some improved image quality and other potentially significant contributions.

SUMMARY OF THE INVENTION

In order to solve the above and other problems, according to a first aspect of the current invention, a method of voltage modulation in dual energy computed tomography (CT), including the steps of: a) generating X ray at a predetermined high energy level and a predetermined low energy level at one or more X-ray tube based upon at least one voltage level applied to the X-ray tube; b) projecting the X ray towards a subject portion; c) modulating the voltage level of at least one of the high energy level and the low energy level applied to the X-ray tube according to attenuation in the subject portion to improve dose efficiency, the dose efficiency being defined by squared signal-to-noise ratio divided by radiation dose; and d) acquiring dual energy data sets at a predetermined total number of projections per rotation (TPPR) as said steps a) through c) are repeated to scan the subject portion.

According to a second aspect of the current invention, a method of voltage modulation in dual energy computed tomography (CT), comprising: generating X ray at two or more energy spectra of X ray including a predetermined high energy level and a predetermined low energy level at one or more X-ray tube based upon at least one voltage level applied to the X-ray tube at one or more current levels through the X-ray tube; projecting the X ray towards a subject portion; acquiring dual energy data sets; modulating the voltage level of at least one of the high energy level and the low energy level according to attenuation in the subject portion and modulating the current level to reduce noise in order to optimize dose efficiency, the dose efficiency being defined by squared signal-to-noise ratio divided by dose; and acquiring other dual energy data sets at a predetermined total number of projections per rotation (TPPR) as the voltage level and the current level are modulated.

According to a third aspect of the current invention, a dual energy computed tomography (CT) system configured to perform voltage modulation during dual energy data acquisition, comprising: one or more X-ray tube configured to generate at least two energy spectra of X ray at a predetermined high level and a predetermined low level based upon at least one voltage level applied to said X-ray tube, said X-ray tube emitting the X ray towards a subject portion; a system controller connected to said X-ray tube for modulating the voltage level of at least one of the high energy level and the low energy level applied to the X-ray tube according to attenuation in the subject portion to improve dose efficiency, and a X-ray detector located opposite from said X-ray tube across the subject portion and configured to detect dual energy data sets at a predetermined total number of projections per rotation (TPPR).

According to a fourth aspect of the current invention, a dual energy computed tomography (CT) system configured to perform voltage modulation during dual energy data acquisition, comprising: one or more X-ray tube configured to generate at two or more energy spectra of X ray including a predetermined high level and a predetermined low level based upon at least one current level applied to said X-ray tube, said X-ray tube projecting the X ray towards a subject portion; a system controller connected to said X ray tube for modulating the voltage level of at least one of the high energy level and the low energy level applied to the X-ray tube according to attenuation in the subject portion and for modulating the current level to reduce noise in order to optimize dose efficiency, the dose efficiency being defined by squared signal-to-noise ratio divided by radiation dose; and a X-ray detector located opposite from said X-ray tube across the subject portion and configured to detect dual energy data sets at a predetermined total number of projections per rotation (TPPR) as the voltage level and the current level are modulated.

According to a fifth aspect of the current invention, a method of voltage modulation in dual energy computed tomography (CT), comprising the steps of: a) generating X-ray at a predetermined high energy level and a predetermined low energy level at one or more X-ray tube based upon at least one voltage level applied to the X ray tube; b) projecting the X ray towards a subject portion; c) modulating the voltage level of at least one of the high energy level and the low energy level applied to the X-ray tube according to attenuation in the subject portion to improve dose efficiency, the dose efficiency being defined by squared signal to noise ratio divided by radiation dose; d) acquiring dual energy data sets at a predetermined total number of projections per rotation (TPPR) as said steps a) through c) are repeated to scan the subject portion; and e) performing data domain decomposition on the dual energy data sets for substantially eliminating beam-hardening artifacts.

According to a sixth aspect of the current invention, a method of voltage modulation in dual energy computed tomography (CT), comprising: generating X ray at two or more energy spectra of X ray including a predetermined high energy level and a predetermined low energy level at one or more X-ray tube based upon at least one voltage level applied to the X ray tube at one or more current levels through the X-ray tube; projecting the X ray towards a subject portion; acquiring dual energy data sets; modulating the voltage level of at least one of the high energy level and the low energy level applied to the X-ray tube according to attenuation in the subject portion and modulating the current level to reduce noise in order to optimize dose efficiency, the dose efficiency being defined by squared signal to noise ratio divided by radiation dose; and acquiring other dual energy data sets at a predetermined total number of projections per rotation (TPPR) as the voltage level and the current level are modulated; and performing data domain decomposition on the dual energy data sets for substantially eliminating beam-hardening artifacts.

According to a seventh aspect of the current invention, a dual energy computed tomography (CT) system configured to perform voltage modulation during dual energy data acquisition, comprising: one or more X-ray tube configured to generate at least two energy spectra of X ray at a predetermined high level and a predetermined low level based upon at least one voltage level applied to said X-ray tube, said X-ray tube emitting the X ray towards a subject portion; a system controller connected to said X-ray tube for modulating the voltage level of at least one of the high energy level and the low energy level applied to the X-ray tube according to attenuation in the subject portion to improve dose efficiency; a X-ray detector located opposite from said X-ray tube across the subject portion and configured to detect dual energy data sets at a predetermined total number of projections per rotation (TPPR); and a preprocessing unit connected to said X-ray detector for performing data domain decomposition on the dual energy data sets for substantially eliminating beam-hardening artifacts.

According to a eighth aspect of the current invention, a dual energy computed tomography (CT) system configured to perform voltage modulation during dual energy data acquisition, comprising: one or more X ray tube configured to generate at two or more energy spectra of X ray including a predetermined high level and a predetermined low level based upon at least one current level applied to said X-ray tube, said X-ray tube projecting the X ray towards a subject portion; a system controller connected to said X ray tube for modulating the voltage level of at least one of the high energy level and the low energy level applied to the X-ray tube according to attenuation in the subject portion and for modulating the current level to reduce noise in order to optimize dose efficiency, the dose efficiency being defined by squared signal to noise ratio divided by radiation dose; a X-ray detector located opposite from said X-ray tube across the subject portion and configured to detect dual energy data sets at a predetermined total number of projections per rotation (TPPR) as the voltage level and the current level are modulated; and a preprocessing unit connected to said X-ray detector for performing data domain decomposition on the dual energy data sets for substantially eliminating beam-hardening artifacts.

These and various other advantages and features of novelty which characterize the invention are pointed out with particularity in the claims annexed hereto and forming a part hereof However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

TABLE 1 summarizes advantages and disadvantages of selected ways to acquire dual energy data sets.

TABLE 2 summarizes optimal values of the photon energy (E), the low and high effective energies (VL, VH) of the spectra and the optimal dose efficiency for density differentiations for subject sizes of 150, 250, 350 and 450 mm.

TABLE 3 summarizes optimal values of the photon energy (E), the low and high effective energies (VL, VH) of the spectra and the optimal dose efficiency for iodine contrast agency differentiations for subject sizes of 150, 250, 350 and 450 mm.

Figure 1:
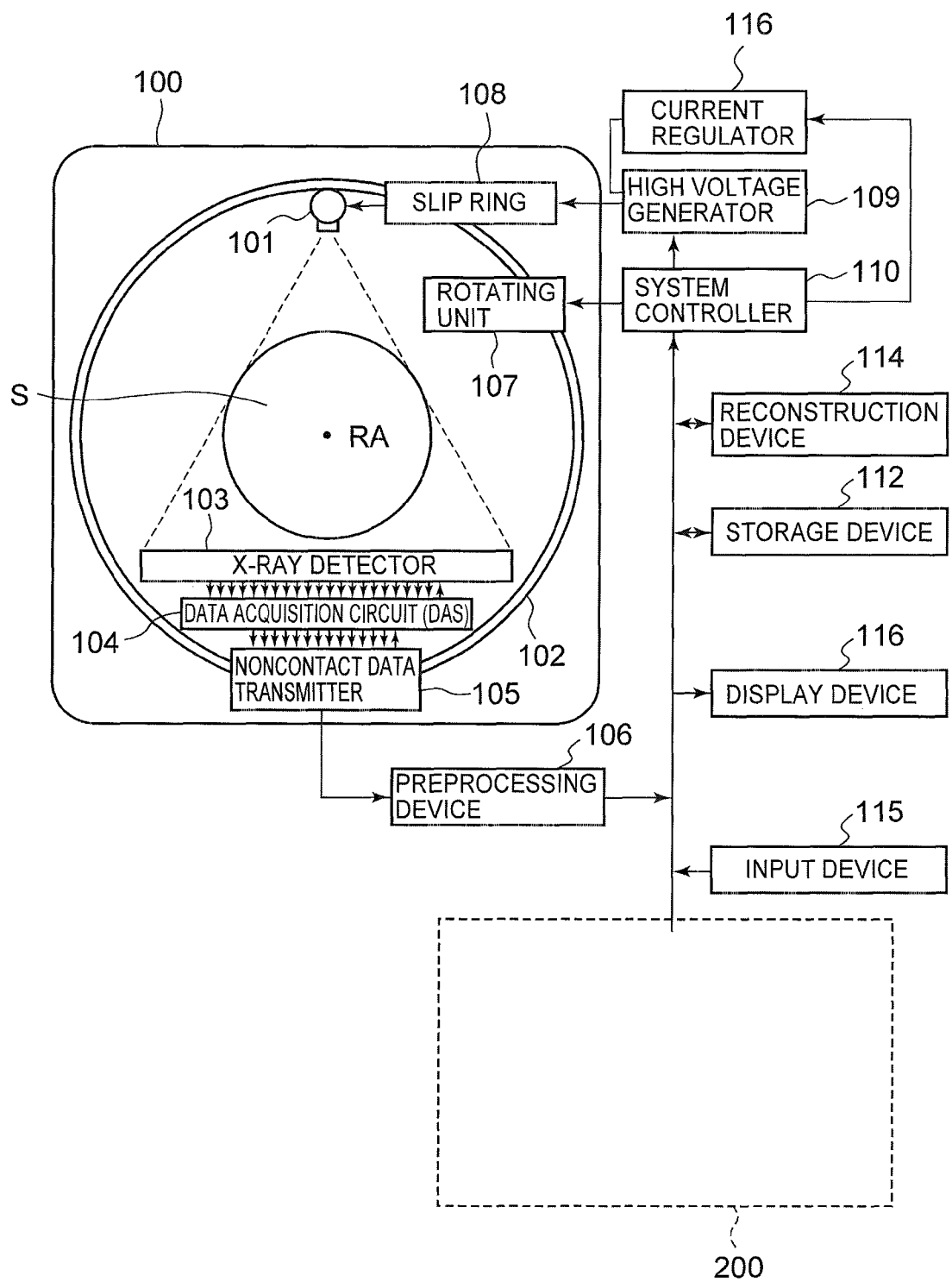

FIG. 1 is a diagram illustrating one embodiment of the CT apparatus according to the current invention.

Figure 2A:
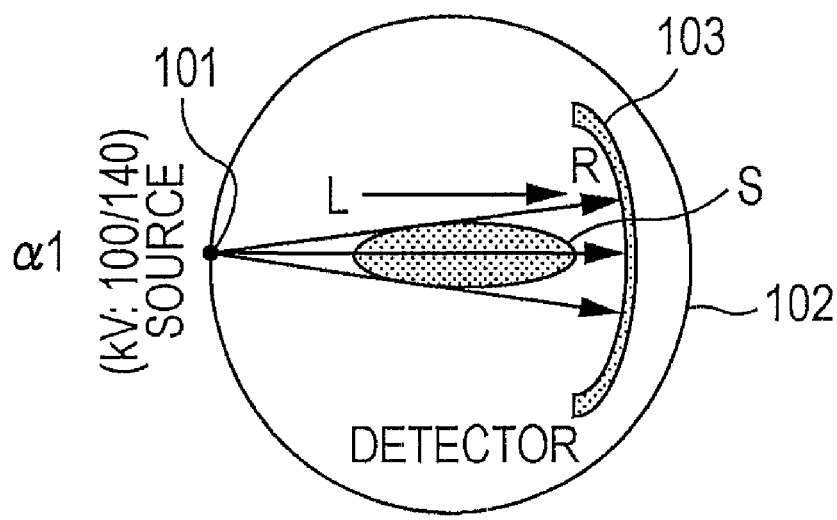
Figure 2B:
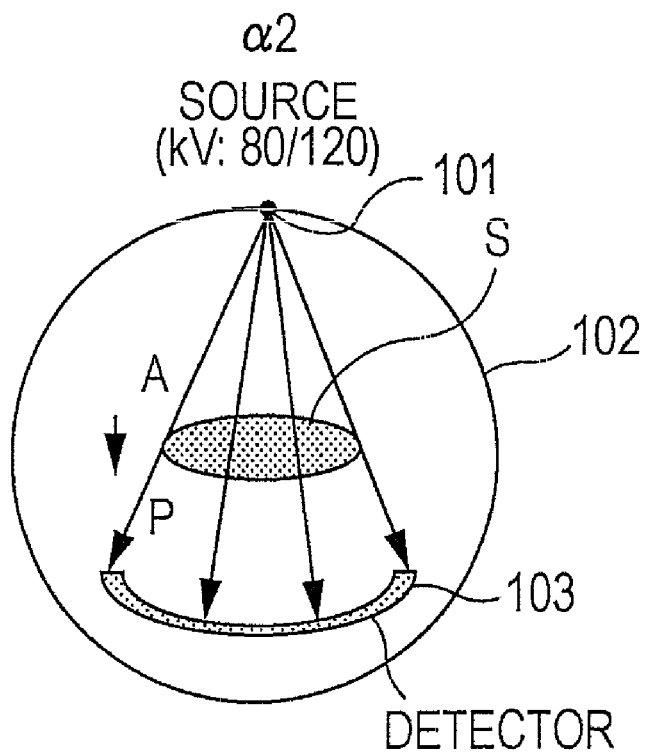

FIGS. 2A and 2B are each a diagram illustrating an exemplary energy levels at a particular view in one embodiment of the CT apparatus according to the current invention.

Figure 3:
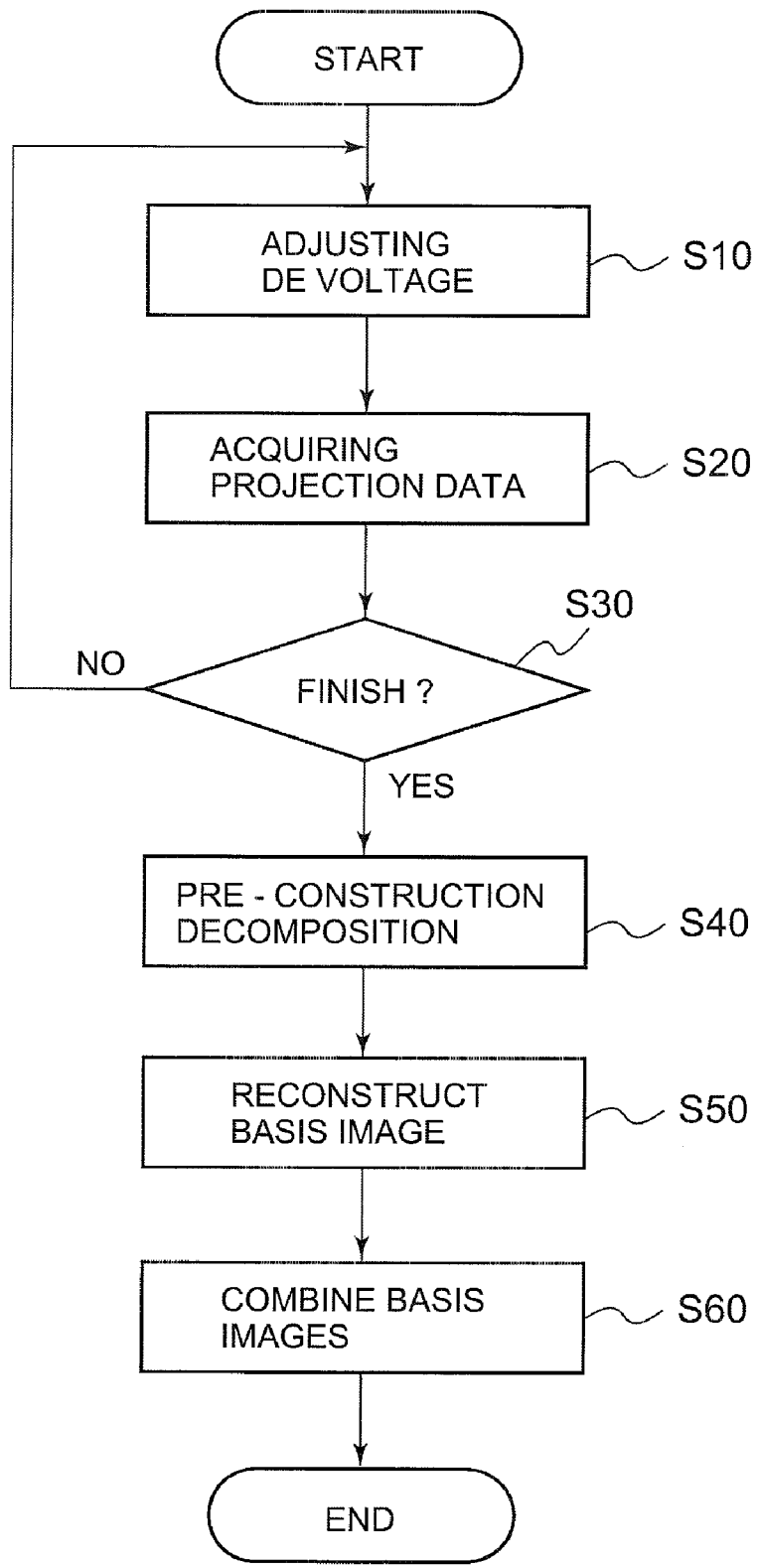

FIG. 3 is a flow chart partially illustrating an exemplary process of voltage modulation in dual energy computed tomography according to one embodiment of the current invention.

FIG. 4 is a flow chart illustrating some exemplary steps of the voltage modulation for dual energy computed tomography according to one embodiment of the present invention.

FIG. 5 is a flow chart illustrating some other exemplary steps of the voltage modulation for dual energy computed tomography according to one embodiment of the present invention.

FIG. 6 is a flow chart illustrating some exemplary steps of the current modulation for dual energy computed tomography according to one embodiment of the present invention.

FIG. 7 is a flow chart illustrating some other exemplary steps of the current modulation for dual energy computed tomography according to one embodiment of the present invention.

Figure 8:
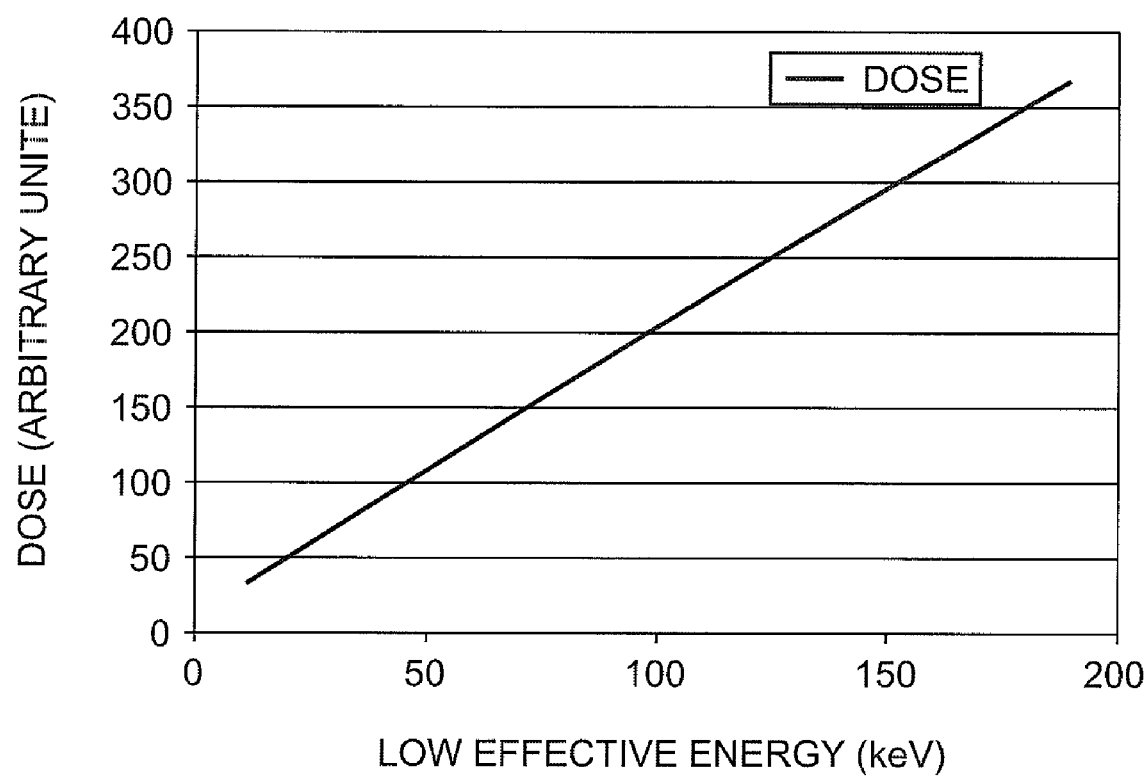

FIG. 8 is a graph illustrating that radiation dose in the one view model is almost linear to effective energy.

Figure 9:
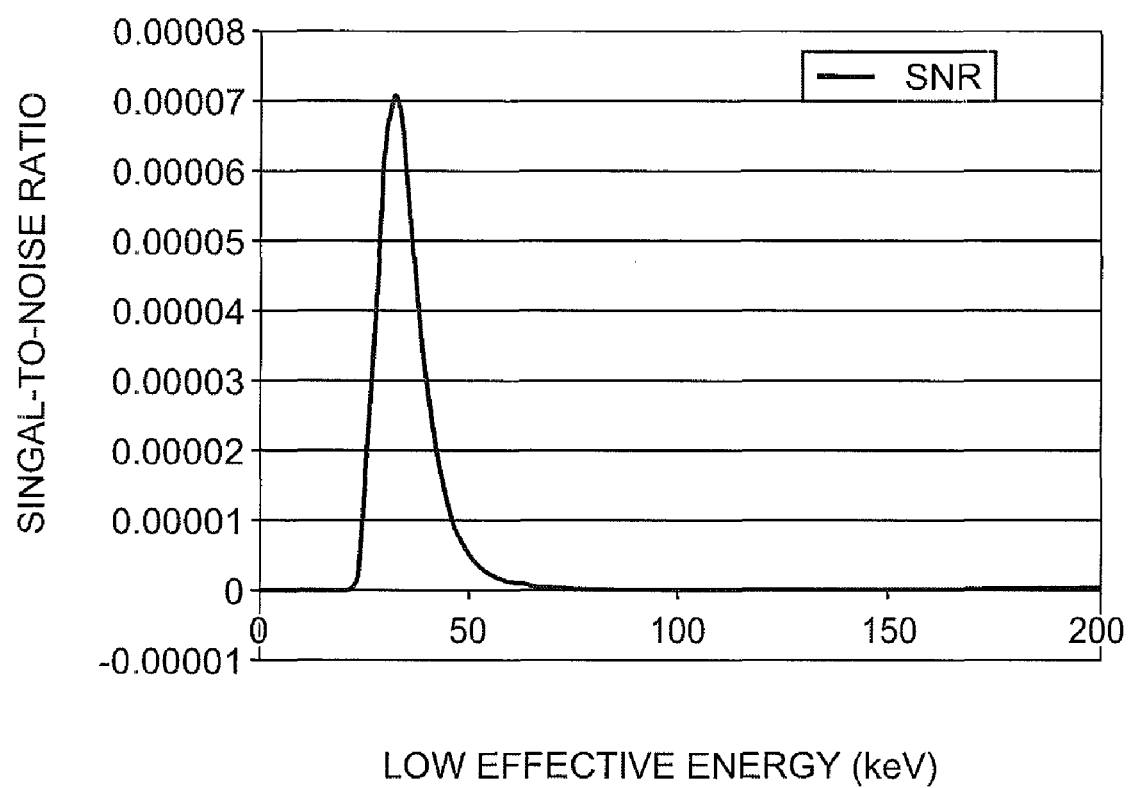

FIG. 9 is a graph illustrating signal to noise ratio in the one view model wherein the contrast is calcium and the background is water.

Figure 10:
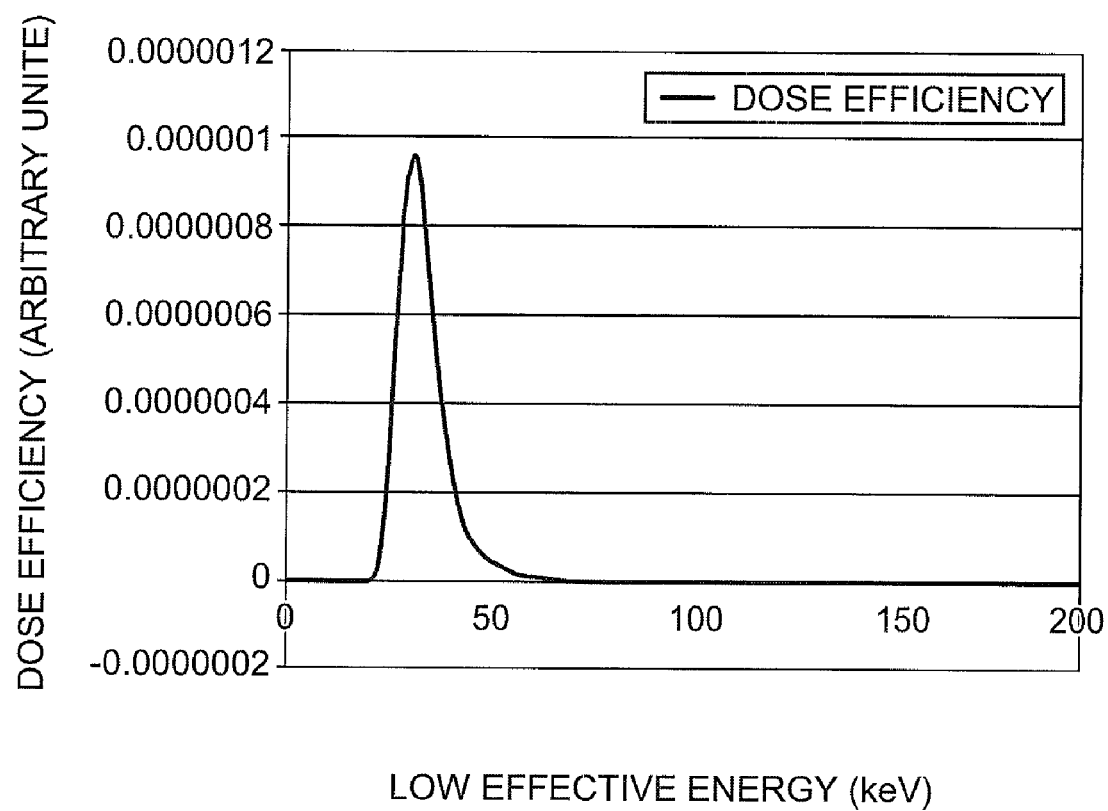
Figure 11A:
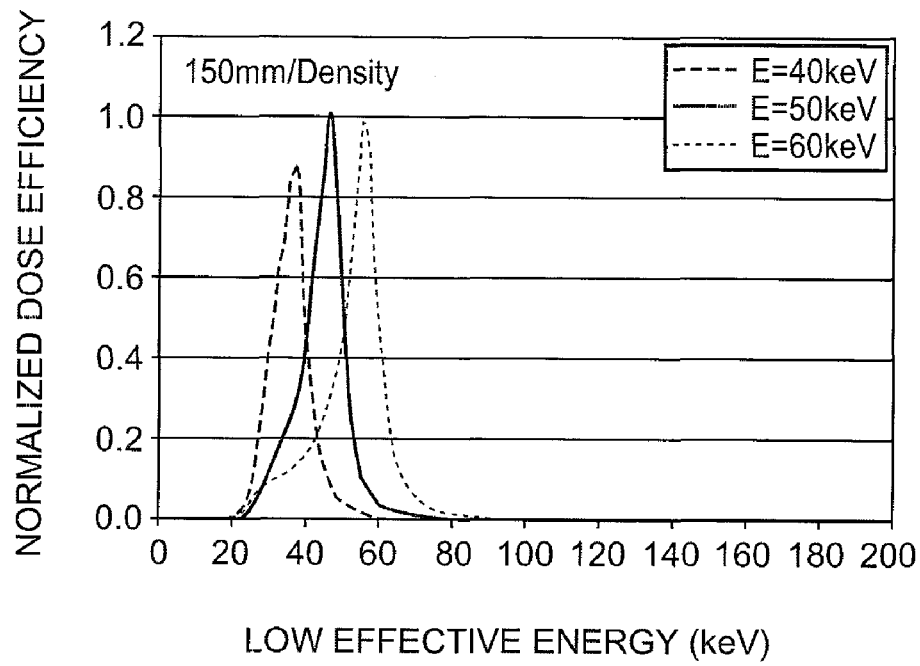
Figure 11B:
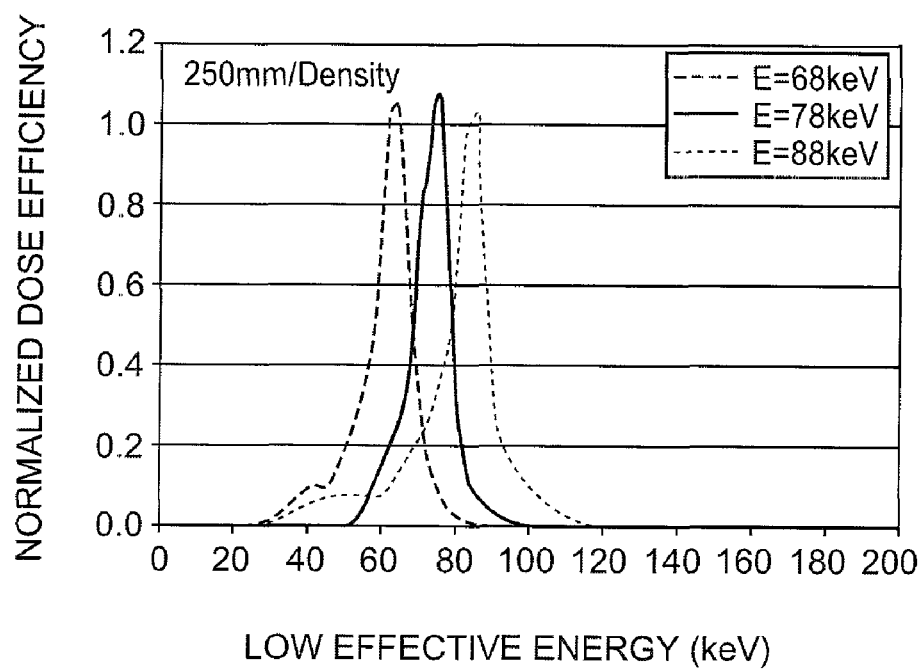
Figure 11C:
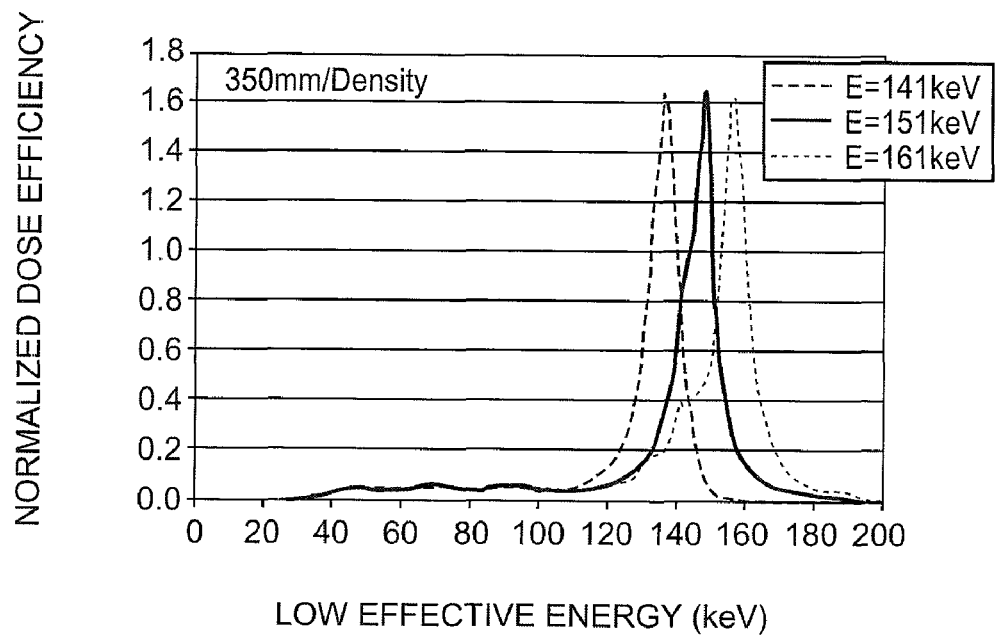
Figure 11D:
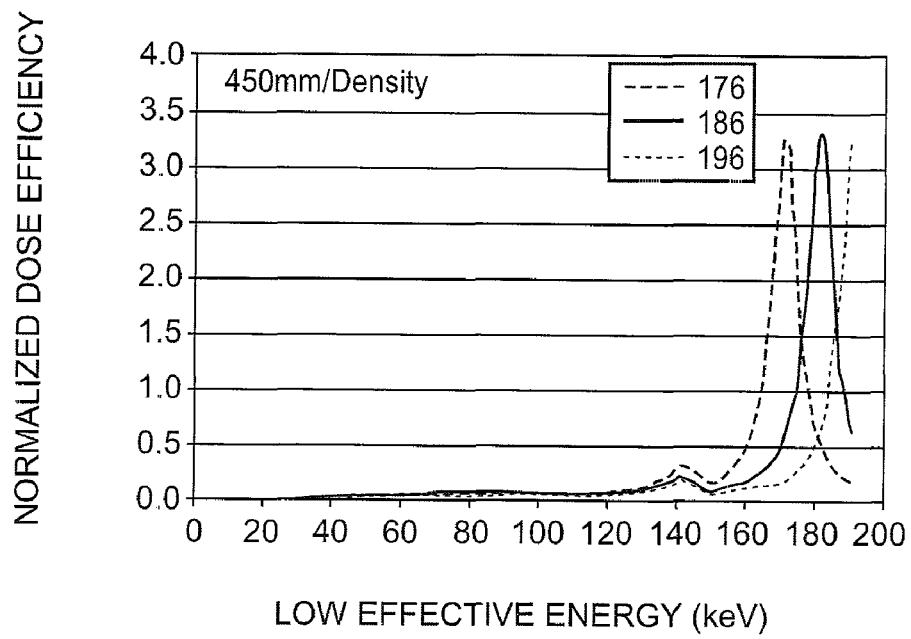
Figure 12A:
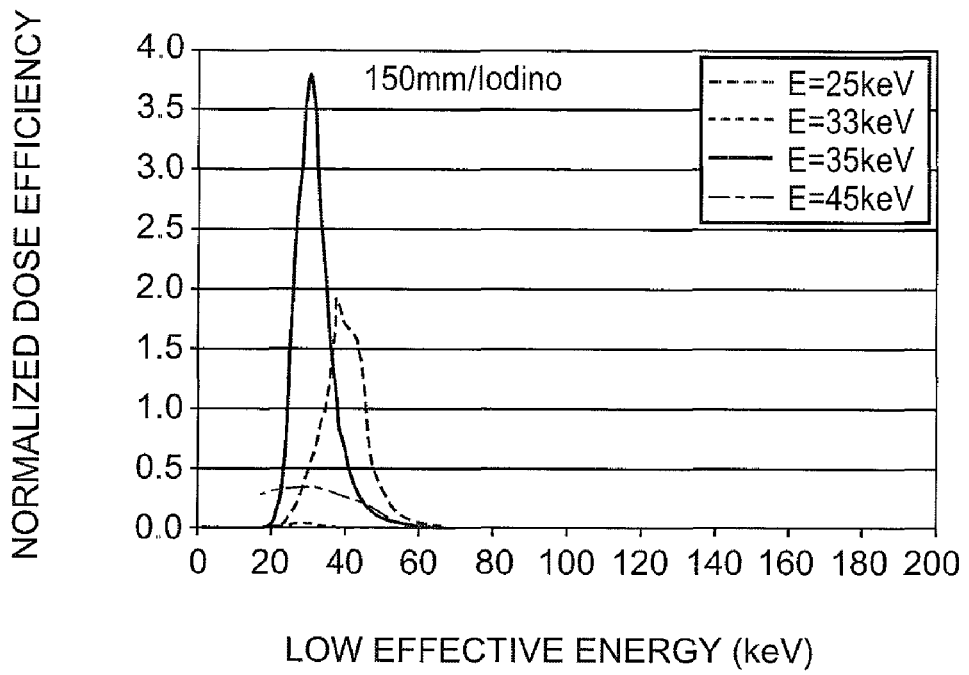
Figure 12B:
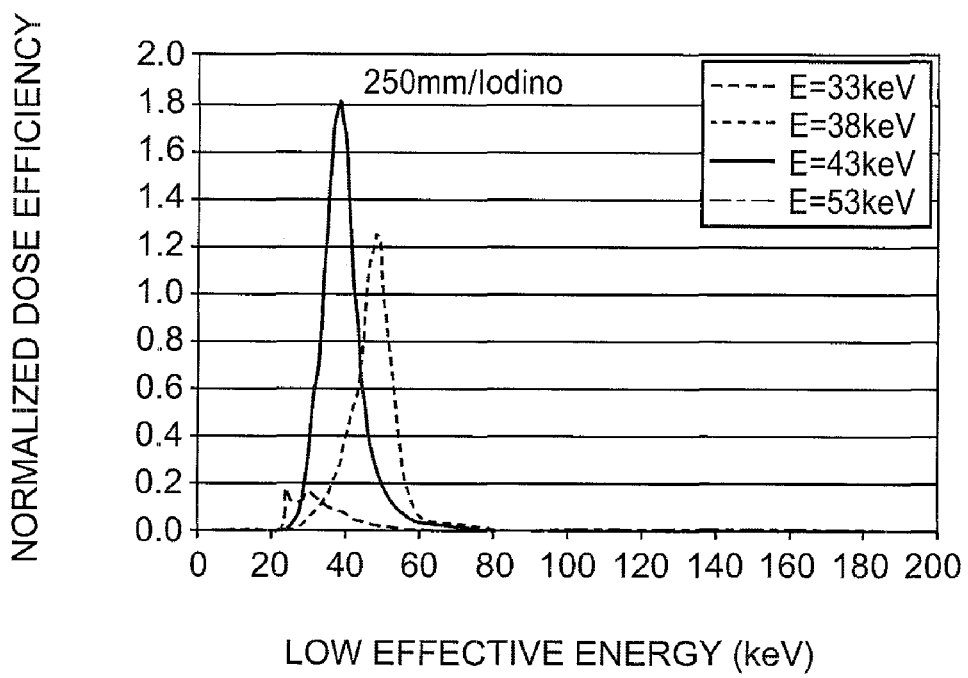
Figure 12C:
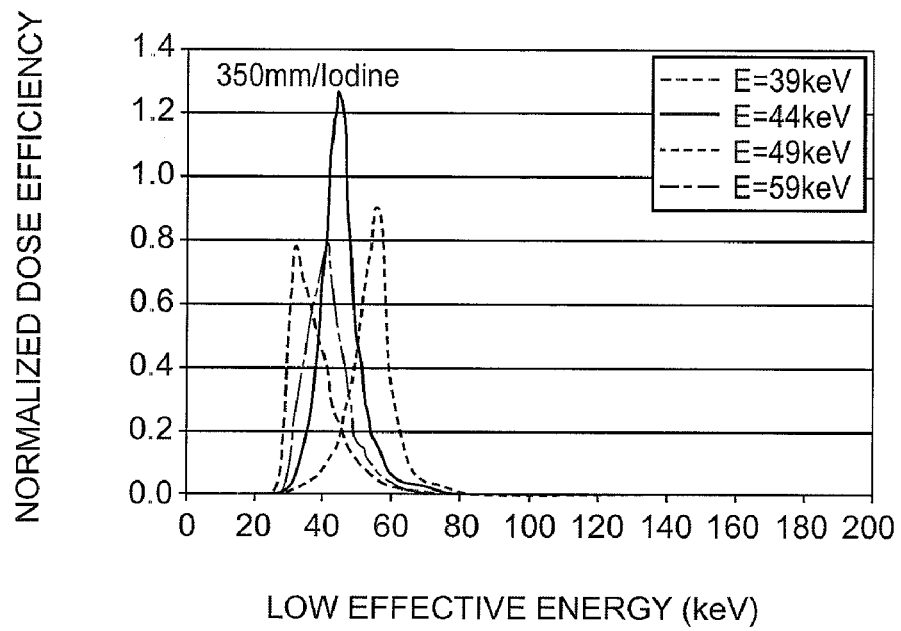
Figure 12D:
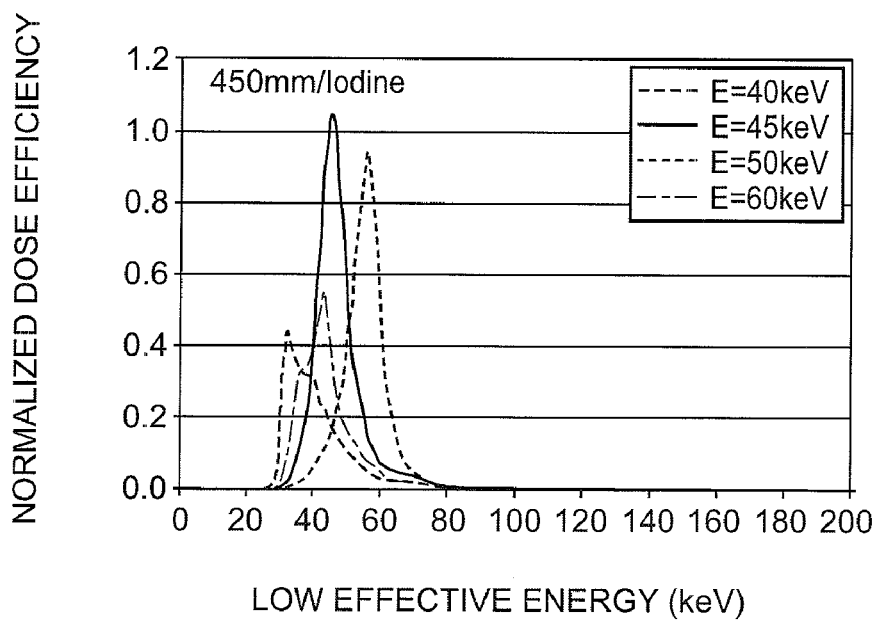

FIG. 10 is a graph illustrating dose efficiency in the one view model where the contrast is calcium and the background is water.

FIGS. 11A through 11D are graphs illustrating the normalized dose efficiency for density differentiation in dual energy CT respectively for subject sizes of 150, 250, 350 and 450 mm.

FIGS. 12A through 12D are graphs illustrating the normalized dose efficiency for iodine contrast agent differentiation in dual energy CT respectively for subject sizes of 150, 250, 350 and 450 mm.

DETAILED DESCRIPTION OF EMBODIMENT(S)

Referring now to the drawings, wherein like reference numerals designate corresponding structures throughout the views, and referring in particular to FIG. 1, a diagram illustrates one embodiment of the multi-slice dual energy X-ray CT apparatus or scanner according to the current invention including a gantry 100 and other devices. The gantry 100 is illustrated in a side view and further includes an X-ray tube 101 and a multi-row or two-dimensional array type X-ray detector 103. The X-ray tube 101 and X-ray detector 103 are diametrically mounted on an annular frame 102 across a subject S, which is rotatably supported around a rotation axis RA. A rotating unit 107 rotates the frame 102 at a high speed such as 0.4 sec/rotation while the subject S is being moved along the axis RA.

The multi-slice dual energy X-ray CT apparatus further includes a high voltage generator 109 that applies a tube voltage to the X-ray tube 101 and supplies a filament current through a slip ring 108 so that the X-ray tube 101 generates X rays. In one embodiment of the multi-slice X-ray CT apparatus according to the current invention, the voltage value at the X-ray tube 101 is set at either a predetermined high energy level or a predetermined low energy level to generate dual energy X rays. The X rays are emitted towards a subject whose cross sectional area is represented by a circle. The X-ray detector 103 is located at an opposite side from the X-ray tube 101 across the subject for detecting the emitted X-rays that has transmitted through the subject.

Still referring to FIG. 1, the X-ray CT apparatus or scanner further includes other devices for processing the detected signals from X-ray detector 103. A data acquisition circuit or a Data Acquisition System (DAS) 104 converts a signal output from the X-ray detector 103 for each channel into a voltage signal, amplifies it, and further converts it into a digital signal. The X-ray detector 103 and the DAS 104 are configured to handle a predetermined total number of projections per rotation (TPPR) ranges up to at the most 900 TPPR, between 900 TPPR and 1800 TPPR and between 900 TPPR and 3600 TPPR.

The above projection raw data is sent to a preprocessing device 106 housed in a console outside the gantry 100 through a non-contact data transmitter 105. The preprocessing device 106 performs certain corrections such as sensitivity correction on the raw data. A storage device 112 then stores the resultant data that is also called projection data at a stage immediately before reconstruction processing. The storage device 112 is connected to a system controller 110 through a data/control bus, together with a reconstruction device 114, display device 116, input device 115, and the scan plan support apparatus 200. The scan plan support apparatus 200 includes a function for supporting an imaging technician to develop a scan plan.

In various embodiments of the CT apparatus or scanners according to the current invention, the dual energy function is implemented in various manners. For example, one embodiment utilizes a fast kV-switching technique that changes voltages between projections (also called views) so that the odd or even projections respectively correspond to the low or high tube voltage. The prior art fast kV-switching techniques have very good temporal and spatial registrations between corresponding high and low energy projections, which make data domain methods possible and lead to better image quality and flexibility even with helical projections. Certain prior art preconstruction decomposition techniques have addressed disadvantages including a high noise level in the low energy data and inherent one-view misregistration between corresponding high and low energy projections.

Another exemplary embodiment utilizes a slow kV-switching technique. For example, for a circular scan, the tube voltage is at high energy for all views during the first rotation. Then, the tube voltage is switched to low energy before or during the next rotation and maintained for all views during the second rotation. In this regard, slow kV-switching is about a factor of 1000 to 2000 slower than fast kV-switching. Although the slow kV-switching technique does not require additional parts or equipment, dual energy data sets result in poor temporal registration that is off by at least one rotation period as well as poor spatial registration in particular from helical scans.

In three other embodiments, the dual energy implementation requires additional hardware devices or components. In one embodiment according to the current invention, the CT apparatus includes dual X-ray sources for simultaneously generating two spectra of X rays. In another embodiment according to the current invention, the CT apparatus includes a specialized sandwich detector or dual layer detector. Both the dual source CT scanners and the sandwich detector CT scanners must resolve some technical difficulties that are associated with these systems as listed in the table above. Lastly, in the last one of the three other embodiments according to the current invention, the CT apparatus further includes a photon counting detector for counting the photons according to the predetermined separate energy bins. In these three other embodiments including the dual sources, the sandwich detector and the photon counting detector, since additional costs incur, these embodiments may be less cost-effective to obtain dual energy data sets.

According to one aspect of the current invention, the dual energy CT apparatus modulates a tube voltage level at the X-ray tube 101 for generating dual energy X rays. In general, a pair of fixed high and low tube voltages is changed during scanning depending upon a thickness or a distance of a subject portion where the X ray transmits. In one embodiment, the system controller 110 selects a particular pair of a predetermined high energy level and a predetermined low energy level from a set of predetermined pairs of the fixed high and low energy values based upon a configuration of the subject portion. The configuration is generally determined based upon the information obtained from pre-scan scanogram, and the configuration-related information is stored in advance for later retrieval by the system controller 110. One exemplary stored information is in a table format including the view angles and the corresponding pair of tube voltage values for generating appropriate spectra of dual energy X rays.

Now referring to FIGS. 2A and 2B, the system controller 110 in one preferred embodiment selects a particular pair of tube voltage levels so as to generate corresponding high and low energy X rays depending upon the thickness or configuration of the subject portion. When the X-ray tube 101 is positioned at an angle $\alpha 1$ with respect to the subject portion S, X ray must travel from the X-ray tube 101 to the X-ray detector 103 in the left-right (LR) direction over a first distance through the subject S as indicated by the arrows as illustrated in FIG. 2A. On the other hand, when the X-ray tube 101 is positioned at an angle $\alpha 2$ with respect to the subject portion S, X ray must travel from the X-ray tube 101 to the X-ray detector 103 in the anterior-posterior (AP) direction over a second distance through the subject S as indicated by the arrows as illustrated in FIG. 2B. Since the first distance in the LR views is generally much longer than the second distance in the AP views in this particular example, attenuation of the same X ray over the first distance in the LR views is more significant than that over the second distance in the AP views. Consequently, the photon starvation in the LR views may lead to undesirable streak artifacts, especially in the dual energy CT.

Still referring to FIGS. 2A and 2B, the X-ray tube 101 in one embodiment of the current invention generates different spectra of X rays depending a selected pair of tube voltage levels. In response to the application of a high tube voltage pair, the X-ray tube 101 generates dual energy X rays of 100 kV for low energy and 140 kV for high energy when projection data is being collected in the LR views as disclosed in FIG. 2A. Similarly, in the same embodiment of the current invention, in response to the application of a low tube voltage pair, the X-ray tube 101 generates dual energy X rays of 80 kV for low energy and 120 kV for high energy when projection data is being collected in the AP views as disclosed in FIG. 2B. Thus, according to one embodiment of the current invention, the tube voltage modulation in the dual energy CT is exemplified by the above described voltage pair selection depending upon the configuration of the subject portion in order to minimize the X-ray dosage for patient safety.

For the voltage modulation according to the current invention, the number of the prefixed pairs of the tube voltage values is not limited to a particular number such as the two pairs as illustrated in FIGS. 2A and 2B. In general, a larger number of pairs of the tube voltage values is used for the voltage modulation at the X-ray tube 101, more likely the dose efficiency approaches an optimal level. On the other hand, a small number of the tube voltage value pairs makes an embodiment simpler to implement according to the current invention. In any case, in each view, the energy separation between the low and high voltage should be sufficient enough to guarantee a stable decomposition.

Furthermore, for the voltage modulation according to the current invention, the tube voltage values are not limited to predetermined pairs of fixed values as illustrated in FIGS. 2A and 2B. In other words, the tube voltage values may be determined on the fly during the scanning process based upon a certain feed back signal from an X-ray detector. For example, in one embodiment according to the current invention, a pair of the tube voltage values is determined so that an attenuated x-radiation value at the present view angle and position is approximated to an average attenuated x-radiation value at the previously detected view angle and position. In any case, in each view, the energy separation between the low and high voltage should be big enough to guarantee a stable decomposition.

To balance image quality and radiation dose, certain current modulation techniques are utilized in combination with the above described dual energy voltage modulation techniques according to another aspect of the current invention. In each scan, the voltage and current may be modulated independently with respect to views to obtain the required image quality at a minimum radiation dose. As described above, the current modulation is generally useful in controlling the noise level but not the penetration of X-ray beam that relates to the dose efficiency. Roughly speaking, the higher a tube current level is during the projection data acquisition, the lower a noise level becomes in the acquired projection data sets. More precisely, the noise level, variance of the projection data, is inversely proportional to the current level. On the other hand, the tube current is proportional to the dosage to the patient. In this regard, the current modulation may improve image quality and achieve an optimal dosage level in the case of fixed dose efficiency. However, the optimal dosage level can be further reduced by improving the dose efficiency through adjusting the penetration of X-ray beam.

For the current control, referring back to FIG. 1, one embodiment of the dual energy CT apparatus according to the current invention further includes a current regulation unit 116 that controls the current level in a filament of the X-ray tube 101 independent of the voltage level at the X-ray tube 101. For example, the system controller 110 in one embodiment selects a particular pair of tube current levels in addition to the duty ratio between the high and low voltages so as to affect the corresponding high and low energy X rays depending upon the thickness or configuration of the subject portion. As illustrated in FIGS. 2A and 2B, depending upon a view with respect to the subject portion S, the current level is modulated to optimize the noise level in the projection data. Consequently, the X-ray tube 101 in one embodiment of the current invention generates different spectra of X rays at a selected pair of tube current levels. Thus, according to one embodiment of the current invention, the independent tube voltage and or current modulation in the dual energy CT is exemplified by the above described voltage and or current pair selection depending upon the configuration of the subject portion in order to minimize the X ray dosage for patient safety without sacrificing the image quality. In any case, in each view, the energy separation between the low and high voltage should be big enough to guarantee a stable decomposition.

Now referring to FIG. 3, a flow chart partially illustrates an exemplary process of voltage modulation in dual energy computed tomography according to one embodiment of the current invention. Certain aspects of the process of FIG. 3 will be described below with respect to the operation of units or components of the embodiment as illustrated in FIG. 1. In a step S10, the process adjusts or modulates the voltage pair levels that are to be applied to the X-ray tube 101, which generates dual energy X ray. Alternatively, in the step S10, the process adjusts or modulates the single voltage level that is to be applied to the X-ray tube 101, which generates a wide spectrum of X ray to be separated a dual layer detector or a photon counting detector for dual energy. In general, the voltage level for dual energy CT is modulated or adjusted for each view to obtain projection data at improved dose efficiency. A combination of the voltage modulation and the current modulation optimizes the dose level.

As described above, the multi-slice dual energy X-ray CT apparatus or scanner according to the current invention utilizes either one or a certain combination of the dual energy data acquisition techniques including fast kV-switching, slow kV-switching, the dual layer detector, the dual energy sources and the photon counting detector. Consequently, the dual energy CT apparatus includes a single source or dual sources for generating X ray to achieve the dual energy environment. On the other hand, when a single X ray source is utilized for dual energy CT, a single voltage value is modulated for use with the photon counting detector or the dual layer detector. On the other hand, a pair of voltage values is modulated for use with fast kV-switching, slow kV-switching and the dual sources.

Subsequently, corresponding projection data are acquired in a step S20 based upon the modulated voltage values as applied to the X-ray tube 101 and the above described dual energy data acquisition techniques as also illustrated in the exemplary embodiments.

In a step S30, it is determined whether or not the modulated voltage values are further adjusted for an additional projection data acquisition sequence. In other words, the step S30 determines whether or not all the necessary views have been scanned. If it is determined in the step S30 that all of the necessary views have not been scanned, the process goes back to the step S10 and repeats the steps S10 and S20. On the other hand, if it is determined in the step S30 that all of the necessary views have been scanned, the process proceeds to a step S40, where the multi-slice X-ray CT apparatus performs pre-construction decomposition on the acquired projection data in each view in order to calculate the lengths of basis materials or component of basis processes that are independent of spectra. This way, the inconsistency due to voltage variation is avoided while the voltages in each view are adjusted to the subject to achieve the optimal dose efficiency. In a step S50, the basis images are reconstructed from the basis lengths as determined in the step S40. Lastly, in a step S60, the basis images are combined to obtain monochromatic images, density images, effective Z images and so on.

Referring to FIG. 4, a flow chart illustrates some exemplary steps of the voltage modulation for dual energy computed tomography according to one embodiment of the present invention. Certain aspects of the process of FIG. 4 will be described below with respect to the operation of units or components of the embodiment as illustrated in FIG. 1. Assuming that a pair of voltage values is modulated in this illustration, the exemplary process in a step S100 retrieves some scanogram information that is previously stored in the storage device 112. For example, the retrieved information includes a first table containing discrete thickness ranges and the corresponding tube voltage pair values and a second table containing view angles and the corresponding thickness values of the pre-scanned subject portion S. In a step S110, the exemplary process initially selects a thickness value based upon the current view angle in the second table. The exemplary process then selects a pair of tube voltage values based upon the selected thickness value in the first table. Since the above described tables and the selections in the steps S100 and S110 are merely illustrative and do not limit the scope of the current invention as claimed in the claimed section, the tube voltage selection can be implemented in a variety of other ways according to the current invention. In the above illustrative steps in one embodiment, the tube voltage pair values are selected from the previously stored pairs of the predetermined values. After a pair of the appropriate tube voltage values is selected, the system controller 110 applies the selected voltage values to the X-ray tube 101 in a step S120 in order to generate dual energy X ray for the dual energy CT. In one embodiment, the exemplary process repeatedly calls the above described steps S100, S110 and S120 as necessary from the voltage adjustment step S10 of FIG. 3.

Still referring to FIG. 4, the exemplary process determines if current adjustment or modulation is desired in addition to the above described voltage modulation according to the one embodiment of the current invention. If the current modulation is not desired or no indication is made in a step S130, the exemplary process returns to a point where the above described voltage modulation steps were initiated. On the other hand, if the current modulation is desired in the step S130, the exemplary process performs a predetermined set of current modulation steps such as illustrated in FIG. 6 or 7. In the above exemplary process, although it is described that the current adjustment determination is made in the step S130 subsequent to the voltage modulation steps S100, S110 and S120, the described sequence of the steps is merely illustrative. In other words, the current modulation is optionally performed almost simultaneously with the voltage modulation in the projection data acquisition step S20 of FIG. 1.

Referring to FIG. 5, a flow chart illustrates some other exemplary steps of the voltage modulation for dual energy computed tomography according to one embodiment of the present invention. Certain aspects of the process of FIG. 5 will be described below with respect to the operation of units or components of the embodiment as illustrated in FIG. 1. In a step S200, the exemplary process determines the modulated tube voltage value or values on the fly during the scanning process based upon a certain feed back signal from the X-ray detector 103. For example, in one embodiment according to the current invention, a pair of the tube voltage values is determined so that an attenuated x-radiation value at the present view angle and position is approximated to an average attenuated x-radiation value at the previously detected view angle and position. In any case, in each view, the energy separation between the low and high voltage should be big enough to guarantee a stable decomposition. Since the above described on-the-fly determination in the step S200 is merely illustrative and does not limit the scope of the current invention as claimed in the claimed section, the tube voltage determination can be implemented in a variety of other ways according to the current invention. In the above illustrative step in one embodiment, the tube voltage pair values are approximated by taking the previously detected values into account. After a pair of the appropriate tube voltage values is calculated, the system controller 110 applies the calculated voltage values to the X-ray tube 101 in a step S210 in order to generate dual energy X ray for the dual energy CT. In one embodiment, the exemplary process repeatedly calls the above described steps S200 and S210 as necessary from the voltage adjustment step S10 of FIG. 3.

Still referring to FIG. 5, the exemplary process determines if current adjustment or modulation is desired in addition to the above described voltage modulation according to the one embodiment of the current invention. If the current modulation is not desired or no indication is made in a step S220, the exemplary process returns to a point where the above described voltage modulation steps were initiated. On the other hand, if the current modulation is desired in the step S220, the exemplary process performs a predetermined set of current modulation steps such as illustrated in FIG. 6 or 7. In the above exemplary process, although it is described that the current adjustment determination is made in the step S220 subsequent to the voltage modulation steps S200 and S210, the described sequence of the steps is merely illustrative. In other words, the current modulation is optionally performed almost simultaneously with the voltage modulation in the projection data acquisition step S20 of FIG. 3.

Now referring to FIG. 6, a flow chart illustrates some exemplary steps of the current modulation for dual energy computed tomography according to one embodiment of the present invention. Certain aspects of the process of FIG. 6 will be described below with respect to the operation of units or components of the embodiment as illustrated in FIG. 1. In a step S300, the exemplary process retrieves some scanogram information that is previously stored in the storage device 112. For example, the retrieved information includes a first table containing discrete thickness ranges and the corresponding tube current pair values and a second table containing view angles and the corresponding thickness values of the pre-scanned subject portion S. In a step S310, the exemplary process initially selects a thickness value based upon the current view angle in the second table. The exemplary process then selects a pair of tube current values based upon the selected thickness value in the first table. Since the above described tables and the selections in the steps S300 and S310 are merely illustrative and do not limit the scope of the current invention as claimed in the claimed section, the tube current selection can be implemented in a variety of other ways according to the present invention. In the above illustrative steps in one embodiment, the tube current pair values are selected from the previously stored pairs of the predetermined values. After a pair of the appropriate tube current values is selected, the system controller 110 modifies the current level through the X-ray tube 101 to the selected current values in a step S320 in order to generate dual energy X ray for the dual energy CT. In one embodiment, the exemplary process repeatedly calls the above described steps S300, S310 and S320 as necessary from the current adjustment step of FIG. 4 or 5.

Referring to FIG. 7, a flow chart illustrates some other exemplary steps of the current modulation for dual energy computed tomography according to one embodiment of the present invention. Certain aspects of the process of FIG. 7 will be described below with respect to the operation of units or components of the embodiment as illustrated in FIG. 1. In a step S400, the exemplary process determines the modulated tube current value or values on the fly during the scanning process based upon a certain feed back signal from the X-ray detector 103. For example, in one embodiment according to the current invention, a pair of the tube current values is determined so that an attenuated x-radiation value at the present view angle and position is approximated to an average attenuated x-radiation value at the previously detected view angle and position. In any case, in each view, the energy separation between the low and high energy should be big enough to guarantee a stable decomposition. Since the above described on-the-fly determination in the step S400 is merely illustrative and does not limit the scope of the current invention as claimed in the claimed section, the tube current determination can be implemented in a variety of other ways according to the present invention. In the above illustrative step in one embodiment, the tube current pair values are approximated by taking the previously detected values into account. After a pair of the appropriate tube current values is calculated, the system controller 110 modifies the current through the X-ray tube 101 to the calculated current values in a step S410 in order to generate dual energy X ray for the dual energy CT. In one embodiment, the exemplary process repeatedly calls the above described steps S400 and S410 as necessary from the current adjustment step of FIG. 4 or 5.

With respect to the current modulation as described in FIGS. 6 and 7, a range of current may vary. For example, if an X-ray generator has the power ranging from 70 kW to 100 kW and the voltage ranging from 80 kV to 140 kV, the maximum current is about 1250 mA. While the typical current value is about 400 mA for the above example, the current value may be as low as 80 mA.

The following five exemplary embodiments have been considered with respect to the above described exemplary processes according to the current invention to illustrate certain combinations of the dual energy data acquisition techniques and the voltage and or current modulation. These embodiments are illustrative only and do not limit the scope of the current invention as claimed in the claim section. A first embodiment utilizes the voltage modulation in the slow kV-switching dual energy CT where either one of low and high energy scans is followed by the other one of low and high energy scans, and the X-ray source generates two separate spectra of X ray. In each scan the voltage of the X-ray source is independently modulated with respect to views to obtain projection data at improved dose efficiency. Optionally, in each scan the voltage and the current of the X-ray source are each independently modulated with respect to views to obtain the required image quality with reduced noise at optimal dose efficiency. In each view, the energy separation between the low and high voltage should be sufficient enough to guarantee a stable decomposition.

A second embodiment utilizes the voltage modulation in the fast kV-switching dual energy CT where the neighboring views correspond to low energy and high energy acquisitions. The X-ray source generates two separate spectra of X ray. The voltage of the X-ray source is modulated with respect to views to obtain projection data at improved dose efficiency. Optionally, the voltage and the current of the X-ray source are each independently modulated with respect to views to obtain the required image quality with reduced noise at optimal dose efficiency. In the neighboring views, the energy separation between the low and high voltage should be sufficient enough to guarantee a stable decomposition.

A third embodiment utilizes the voltage modulation in the dual energy CT with a dual layer detector where only one, but wide, source spectrum of X ray is required. The first and second layers of the dual layer detector respectively output the low and high energy signals. The voltage of the X-ray source is modulated with respect to views to obtain projection data at improved dose efficiency. Optionally, the voltage and the current of the X-ray source are each independently modulated with respect to views to obtain the required image quality with reduced noise at optimal dose efficiency.

A fourth embodiment utilizes the voltage modulation in the dual energy CT with a photon counting detector by which the photons are counted separately according to the energy bins. The photons are sorted into two groups: low energy and high energy. Similar to dual layer detector dual energy CT, only one, but wide, source spectrum of X ray is required. The voltage of the X-ray source is modulated with respect to views to obtain projection data at improved dose efficiency. Optionally, the voltage and the current of the X-ray source are each independently modulated with respect to views to obtain the required image quality with reduced noise at optimal dose efficiency.

A fifth embodiment utilizes the voltage modulation in the dual source dual energy CT. The two X-ray sources generate two separate spectra of X ray. In a dual source dual energy, it is assumed that the projection data from the two sources are aligned ray by ray for each view. Based upon the assumption, a pre-reconstruction decomposition is possible after a dual energy scan where one source has a low voltage and the other has a high voltage. The voltages of the two X-ray sources is independently modulated with respect to views to obtain projection data at improved dose efficiency. Optionally, the voltages and the current of the two X-ray sources are each modulated with respect to views to obtain the required image quality with reduced noise at optimal dose efficiency.

In the above described embodiments, the voltage is optionally selected to vary discretely or continuously in the voltage modulation. In the discrete voltage modulation, a predetermined number of discrete voltages values is used. In other words, the voltage or voltage pair is changed for views with different attenuation. On the other hand, in the continuous voltage modulation, the voltage may vary continuously with respect to views.

As already described above, the voltage modulation is optionally combined with the current modulation. The combined voltage and current modulation achieves optimal dose efficiency and noise level while the use of either of the two modulations reduces the dose but may not achieve both the optimal dose efficiency level and the optimal noise level in most cases. In this regard, the relationship will be further described among radiation dose, signal to noise ratio and dose efficiency with respect to one view model. The one view model is utilized to determine the optimal dose efficiency for each view in order to approximate an overall optimal dose efficiency for multiple views.

Radiation dose Q can be estimated as $$Q \approx \sum_\lambda \left\{ \begin{array}{l} V_\lambda^{(L)} N_\lambda^{(L)} [1 - \exp(-p_\lambda(V_\lambda^{(L)}))] + \\ V_\lambda^{(H)} N_\lambda^{(H)} [1 - \exp(-p_\lambda(V_\lambda^{(H)}))] \end{array} \right\},$$

where $\lambda$ is the view index, $V_\lambda^{(L)}$ and $V_\lambda^{(H)}$ are effective energy for the X-ray spectra with the low and high voltages, $N_\lambda^{(L)}$ and $N_\lambda^{(H)}$ indicate the incident photon numbers, and $p_\lambda(V_\lambda^{(L)})$ and $p_\lambda(V_\lambda^{(H)})$ represent average attenuation in view $\lambda$. Note that the effective energy can be related to voltage. In general, effective energy is non-linear to voltage but roughly we can think that voltage=2*(effective energy). As shown in FIG. 8, radiation dose in the one view model is almost linear to effective energy because the exponential factor is close to zero.

The square of signal to noise ratio SNR² can be expressed as, $$SNR^2 = \frac{[\mu_C(E) - \mu_B(E)]^2}{\sum_\lambda \sigma^2(E, V_\lambda^{(L)}, V_\lambda^{(H)})},$$

where $\mu_C(E)$ and $\mu_B(E)$ are linear attenuation coefficients of contrast and background at photon energy E, and $$\sigma^2(E, V_\lambda^{(L)}, V_\lambda^{(H)}) = \frac{R^2 \exp(p_\lambda(V_\lambda^{(L)}))}{Det^2 \cdot N_\lambda^{(L)}} \left[ \frac{\mu_1(E)\mu_2(V_\lambda^{(H)}) -}{\mu_2(E)\mu_1(V_\lambda^{(L)})} \right]^2 +$$

$$\frac{R^2 \exp(p_\lambda(V_\lambda^{(H)}))}{Det^2 \cdot N_\lambda^{(H)}} \left[ \frac{\mu_2(E)\mu_1(V_\lambda^{(L)}) -}{\mu_1(E)\mu_2(V_\lambda^{(H)})} \right]^2,$$

$$Det^2 = [\mu_1(V_\lambda^{(L)})\mu_2(V_\lambda^{(H)}) - \mu_2(V_\lambda^{(L)})\mu_1(V_\lambda^{(H)})]^2.$$

where constant R relates to the reconstruction operator. FIG. 9 illustrates signal to noise ratio in the one view model wherein the contrast is calcium and the background is water.

The dose efficiency r can be defined as, $$r = \frac{SNR^2}{Q}.$$

In the one view model, $$r = \frac{[\mu_C(E) - \mu_B(E)]}{\sigma^2(E, V_\lambda^{(L)}, V_\lambda^{(H)}) \left\{ \begin{array}{l} V_\lambda^{(L)} N_\lambda^{(L)}[1 - \exp(-p_\lambda(V_\lambda^{(L)}))] + \\ V_\lambda^{(H)} N_\lambda^{(H)}[1 - \exp(-p_\lambda(V_\lambda^{(H)}))] \end{array} \right\}}$$

FIG. 10 illustrates dose efficiency in the one view model where the contrast is calcium and the background is water. Although the effective energy value at the peak dose efficiency in FIG. 10 is in the vicinity of the effective energy value at the peak signal to noise ratio in FIG. 9, their values are different. Consequently, the corresponding voltage values are also different for the peak signal to noise ratio and the peak dose efficiency.

Now referring to FIGS. 11A through 11D and TABLE 2, the four graphs illustrate the normalized dose efficiency for density differentiation in dual energy CT respectively for subject sizes of 150, 250, 350 and 450 mm. In each subject portions, water is assumed as the background, and the energy separation is fixed as 9 keV. The dose efficiency was normalized to the standard scan voltage of 120 kV in single energy CT where the effective energy was approximately 57 keV. TABLE 2 summarizes optimal values of the photon energy (E), the low and high effective energies (VL, VH) of the spectra and the optimal dose efficiency for density differentiations for subject sizes of 150, 250, 350 and 450 mm.

As shown in FIGS. 11A through 11D and also summarized in TABLE 2, the optimal effective energy increases rapidly with respect to the subject size. For small subjects of 150 nm and 250 nm in diameter, the maximum dose efficiency is slightly higher than that of the standard scan voltage of 120 kV. For large subject of 450 nm in diameter, the optimal dose efficiency could be as high as 3.37 times from that of the standard scan voltage of 120 kV.

FIGS. 12A through 12D are graphs illustrating the normalized dose efficiency for iodine contrast agent (ICA) differentiation in dual energy CT respectively for subject sizes of 150, 250, 350 and 450 mm. In each subject portions, water is assumed as the background, and the energy separation is fixed as 9 keV. The dose efficiency was normalized to the standard scan voltage of 120 kV in single energy CT where the effective energy was approximately 57 keV. TABLE 3 summarizes optimal values of the photon energy (E), the low and high effective energies (VL, VH) of the spectra and the optimal dose efficiency for iodine contrast agency differentiations for subject sizes of 150, 250, 350 and 450 mm.

As shown in FIGS. 12A through 12D and also summarized in TABLE 3, the optimal effective energy increases slowly with respect to the subject size. For a small subject of 150 nm in diameter, the maximum dose efficiency is as high as 3.8 of that from the standard scan voltage of 120 kV. On the other hand, for a large subject of 450 nm in diameter, the optimal dose efficiency is as low as 1.05 times from that of the standard scan voltage of 120 kV.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

TABLE 2

| SIZE (mm) | E (keV) | VL (keV) | VH (keV) | r (norm.) |
|---|---|---|---|---|
| 150 | 50 | 46 | 55 | 1.01 |
| 250 | 78 | 74 | 83 | 1.08 |
| 350 | 151 | 148 | 157 | 1.64 |
| 450 | 196 | 191 | 200 | 3.37 |

TABLE 3

| SIZE (mm) | E (keV) | VL (keV) | VH (keV) | r (norm.) |
|---|---|---|---|---|
| 150 | 35 | 30 | 39 | 3.80 |
| 250 | 43 | 38 | 47 | 1.81 |
| 350 | 49 | 44 | 53 | 1.26 |
| 450 | 50 | 45 | 54 | 1.05 |

What is claimed is:

1. A method of voltage modulation in dual energy computed tomography (CT), comprising the steps of:
    a) generating X ray at a predetermined high energy level and a predetermined low energy level at one or more X-ray tube based upon at least one voltage level applied to the X ray tube;
    b) projecting the X ray towards a subject portion;
    c) modulating the voltage level of at least one of the high energy level and the low energy level applied to the X-ray tube according to attenuation in the subject portion to improve dose efficiency, the dose efficiency being defined by squared signal to noise ratio divided by radiation dose; and
    d) acquiring dual energy data sets at a predetermined total number of projections per rotation (TPPR) as said steps a) through c) are repeated to scan the subject portion.

2. The method of voltage modulation according to claim 1 wherein the dual energy is accomplished by fast kv-switching and two of the voltage levels are alternately applied to the X-ray tube for each of the projections.

3. The method of voltage modulation according to claim 1 wherein the attenuation in said step c) is determined in advance of said step a).

4. The method of voltage modulation according to claim 3 wherein the attenuation is determined by scanogram.

5. The method of voltage modulation according to claim 1 wherein the attenuation in said step c) is determined on the fly.

6. The method of voltage modulation according to claim 1 further comprising an additional step of modulating a current level prior to said step d) to further reduce a noise level in the dual energy data sets in order to optimize the improved dose efficiency.

7. The method of voltage modulation according to claim 6 wherein the current level is modulated by selecting a current value from a set of predetermined current values.

8. The method of voltage modulation according to claim 6 wherein the current level is modulated by selecting a pair of current values from a set of predetermined current pair values.

9. The method of voltage modulation according to claim 6 wherein the current level is determined based upon scanogram.

10. The method of voltage modulation according to claim 6 wherein the current level is determined on the fly.

11. The method of voltage modulation according to claim 6 wherein the voltage level and the current level are independently modulated.

12. A method of voltage modulation in dual energy computed tomography (CT), comprising:
- generating X ray at two or more energy spectra of X ray including a predetermined high energy level and a predetermined low energy level at one or more X-ray tube based upon at least one voltage level applied to the X-ray tube at one or more current levels through the X-ray tube;
- projecting the X ray towards a subject portion;
- acquiring dual energy data sets;
- modulating the voltage level of at least one of the high energy level and the low energy level applied to the X-ray tube according to attenuation in the subject portion and modulating the current level to reduce noise in order to optimize dose efficiency, the dose efficiency being defined by squared signal to noise ratio divided by radiation dose; and
- acquiring other dual energy data sets at a predetermined total number of projections per rotation (TPPR) as the voltage level and the current level are modulated.

13. The method of voltage modulation according to claim 12 wherein the voltage level and the current level are independently modulated.

14. A dual energy computed tomography (CT) system configured to perform voltage modulation during dual energy data acquisition, comprising:
- one or more X-ray tube configured to generate at least two energy spectra of X ray at a predetermined high level and a predetermined low level based upon at least one voltage level applied to said X-ray tube, said X-ray tube emitting the X ray towards a subject portion;
- a system controller connected to said X-ray tube for modulating the voltage level of at least one of the high energy level and the low energy level applied to the X-ray tube according to attenuation in the subject portion to improve dose efficiency; and
  - a X-ray detector located opposite from said X-ray tube across the subject portion and configured to detect dual energy data sets at a predetermined total number of projections per rotation (TPPR).

15. The dual energy computed tomography (CT) system according to claim 14 wherein said X-ray tube generates the dual energy by fast kv-switching and two of the voltage levels are alternately applied to said X-ray tube for each of the projections.

16. The dual energy computed tomography (CT) system according to claim 14 wherein the dose efficiency being defined by squared signal to noise ratio divided by radiation dose.

17. The dual energy computed tomography (CT) system according to claim 14 wherein the attenuation is determined in advance.

18. The dual energy computed tomography (CT) system according to claim 14 wherein the attenuation is determined by scanogram.

19. The dual energy computed tomography (CT) system according to claim 14 wherein said system controller determines the attenuation on the fly.

20. The dual energy computed tomography (CT) system according to claim 14 further comprising a current regulator connected to said system controller and said X-ray tube for modulating a current level to further reduce a noise level in the dual energy data set in order to optimize the improved dose efficiency.

21. The dual energy computed tomography (CT) system according to claim 20 wherein said system controller modulates the current level by selecting a current value from a set of predetermined current values.

22. The dual energy computed tomography (CT) system according to claim 20 wherein said system controller modulates the current level by selecting a pair of current values from a set of predetermined current pair values.

23. The dual energy computed tomography (CT) system according to claim 20 wherein the current level is determined based upon scanogram.

24. The dual energy computed tomography (CT) system according to claim 20 wherein the current level is determined on the fly.

25. The dual energy computed tomography (CT) system according to claim 20 wherein the voltage level and the current level are independently modulated.

26. A dual energy computed tomography (CT) system configured to perform voltage modulation during dual energy data acquisition, comprising:
- one or more X ray tube configured to generate at two or more energy spectra of X ray including a predetermined high level and a predetermined low level based upon at least one current level applied to said X-ray tube, said X-ray tube projecting the X ray towards a subject portion;
- a system controller connected to said X ray tube for modulating the voltage level of at least one of the high energy level and the low energy level applied to the X-ray tube according to attenuation in the subject portion and for modulating the current level to reduce noise in order to optimize dose efficiency, the dose efficiency being defined by squared signal to noise ratio divided by radiation dose; and
- a X-ray detector located opposite from said X-ray tube across the subject portion and configured to detect dual energy data sets at a predetermined total number of projections per rotation (TPPR) as the voltage level and the current level are modulated.

27. The dual energy computed tomography (CT) system according to claim 26
- wherein the voltage level and the current level are independently modulated.

28. A method of voltage modulation in dual energy computed tomography (CT), comprising the steps of:
- a) generating X-ray at a predetermined high energy level and a predetermined low energy level at one or more X-ray tube based upon at least one voltage level applied to the X ray tube;
- b) projecting the X ray towards a subject portion;
- c) modulating the voltage level of at least one of the high energy level and the low energy level applied to the X-ray tube according to attenuation in the subject portion to improve dose efficiency, the dose efficiency being defined by squared signal to noise ratio divided by radiation dose;
- d) acquiring dual energy data sets at a predetermined total number of projections per rotation (TPPR) as said steps a) through c) are repeated to scan the subject portion; and
- e) performing data domain decomposition on the dual energy data sets for substantially eliminating beam-hardening artifacts.

29. A method of voltage modulation in dual energy computed tomography (CT), comprising:
- generating X ray at two or more energy spectra of X ray including a predetermined high energy level and a predetermined low energy level at one or more X-ray tube based upon at least one voltage level applied to the X ray tube at one or more current levels through the X-ray tube;

projecting the X ray towards a subject portion;

acquiring dual energy data sets;

modulating the voltage level of at least one of the high energy level and the low energy level applied to the X-ray tube according to attenuation in the subject portion and modulating the current level to reduce noise in order to optimize dose efficiency, the dose efficiency being defined by squared signal to noise ratio divided by radiation dose; and acquiring other dual energy data sets at a predetermined total number of projections per rotation (TPPR) as the voltage level and the current level are modulated; and performing data domain decomposition on the dual energy data sets for substantially eliminating beam-hardening artifacts.

30. A dual energy computed tomography (CT) system configured to perform voltage modulation during dual energy data acquisition, comprising:

one or more X-ray tube configured to generate at least two energy spectra of X ray at a predetermined high level and a predetermined low level based upon at least one voltage level applied to said X-ray tube, said X-ray tube emitting the X ray towards a subject portion;

a system controller connected to said X-ray tube for modulating the voltage level of at least one of the high energy level and the low energy level applied to the X-ray tube according to attenuation in the subject portion to improve dose efficiency;

a X-ray detector located opposite from said X-ray tube across the subject portion and configured to detect dual energy data sets at a predetermined total number of projections per rotation (TPPR); and a preprocessing unit connected to said X-ray detector for performing data domain decomposition on the dual energy data sets for substantially eliminating beam-hardening artifacts.

31. A dual energy computed tomography (CT) system configured to perform voltage modulation during dual energy data acquisition, comprising:

one or more X ray tube configured to generate at two or more energy spectra of X ray including a predetermined high level and a predetermined low level based upon at least one current level applied to said X-ray tube, said X-ray tube projecting the X ray towards a subject portion;

a system controller connected to said X ray tube for modulating the voltage level of at least one of the high energy level and the low energy level applied to the X-ray tube according to attenuation in the subject portion and for modulating the current level to reduce noise in order to optimize dose efficiency, the dose efficiency being defined by squared signal to noise ratio divided by radiation dose;

a X-ray detector located opposite from said X-ray tube across the subject portion and configured to detect dual energy data sets at a predetermined total number of projections per rotation (TPPR) as the voltage level and the current level are modulated; and a preprocessing unit connected to said X-ray detector for performing data domain decomposition on the dual energy data sets for substantially eliminating beam-hardening artifacts.

* * * * *